United States Patent
Cochran et al.

[11] Patent Number: 5,365,084
[45] Date of Patent: Nov. 15, 1994

[54] VIDEO INSPECTION SYSTEM EMPLOYING MULTIPLE SPECTRUM LED ILLUMINATION

[75] Inventors: Don W. Cochran; James E. Triner, both of Gates Mills, Ohio

[73] Assignee: Pressco Technology, Inc., Solon, Ohio

[21] Appl. No.: 990,009

[22] Filed: Dec. 14, 1992

Related U.S. Application Data

[63] Continuation-in-part of Ser. No. 658,093, Feb. 20, 1991, Pat. No. 5,172,005.

[51] Int. Cl.⁵ ............ G01N 21/86; H04N 7/18
[52] U.S. Cl. ............ 250/571; 250/226; 356/430; 348/88
[58] Field of Search ............ 250/560, 561, 562, 571, 250/572, 226, 234, 235, 236; 356/376, 379, 380, 386, 387, 430, 431, 434, 435; 358/101, 106

[56] References Cited

U.S. PATENT DOCUMENTS

| | | | |
|---|---|---|---|
| 4,882,498 | 11/1989 | Cochran et al. | 250/571 |
| 4,888,480 | 12/1989 | Dakin et al. | 250/226 |
| 4,922,337 | 5/1990 | Hunt et al. | 358/101 |
| 4,949,172 | 8/1990 | Hunt et al. | 358/101 |
| 5,021,645 | 6/1991 | Satula et al. | 250/226 |
| 5,040,057 | 8/1991 | Gilblom et al. | 358/101 |
| 5,060,065 | 10/1991 | Wasserman | 358/101 X |
| 5,072,128 | 12/1991 | Hayano et al. | 250/226 X |
| 5,087,822 | 2/1992 | Fairlie et al. | 250/572 |
| 5,172,005 | 12/1992 | Cochran et al. | 250/571 |
| 5,197,105 | 3/1993 | Uemura et al. | 382/8 |

Primary Examiner—David C. Nelms
Assistant Examiner—John R. Lee
Attorney, Agent, or Firm—Fay, Sharpe, Beall, Fagan, Minnich & McKee

[57] ABSTRACT

An engineered lighting system for high speed video inspection includes an array of light emitting diodes including light emitting diodes for use in time delay integration (TDI) inspection of web materials. The light emitting diodes of the array are selectively controllable to accomplish sequential illumination and carefully controllable imaging of a specified section of a continuously moving specimen or specimens. LEDs with different wavelength light output, or multi-wavelength light LEDs are utilized for rapid and reliable inspection of surfaces with varying color or contour or detect characteristics. The system also includes an array of optional backlighting elements to aid in illumination of semi-opaque specimens to accomplish inspection thereof.

39 Claims, 9 Drawing Sheets

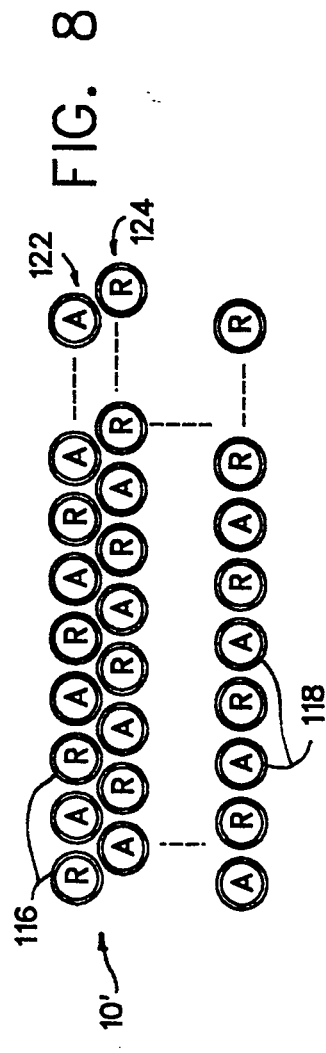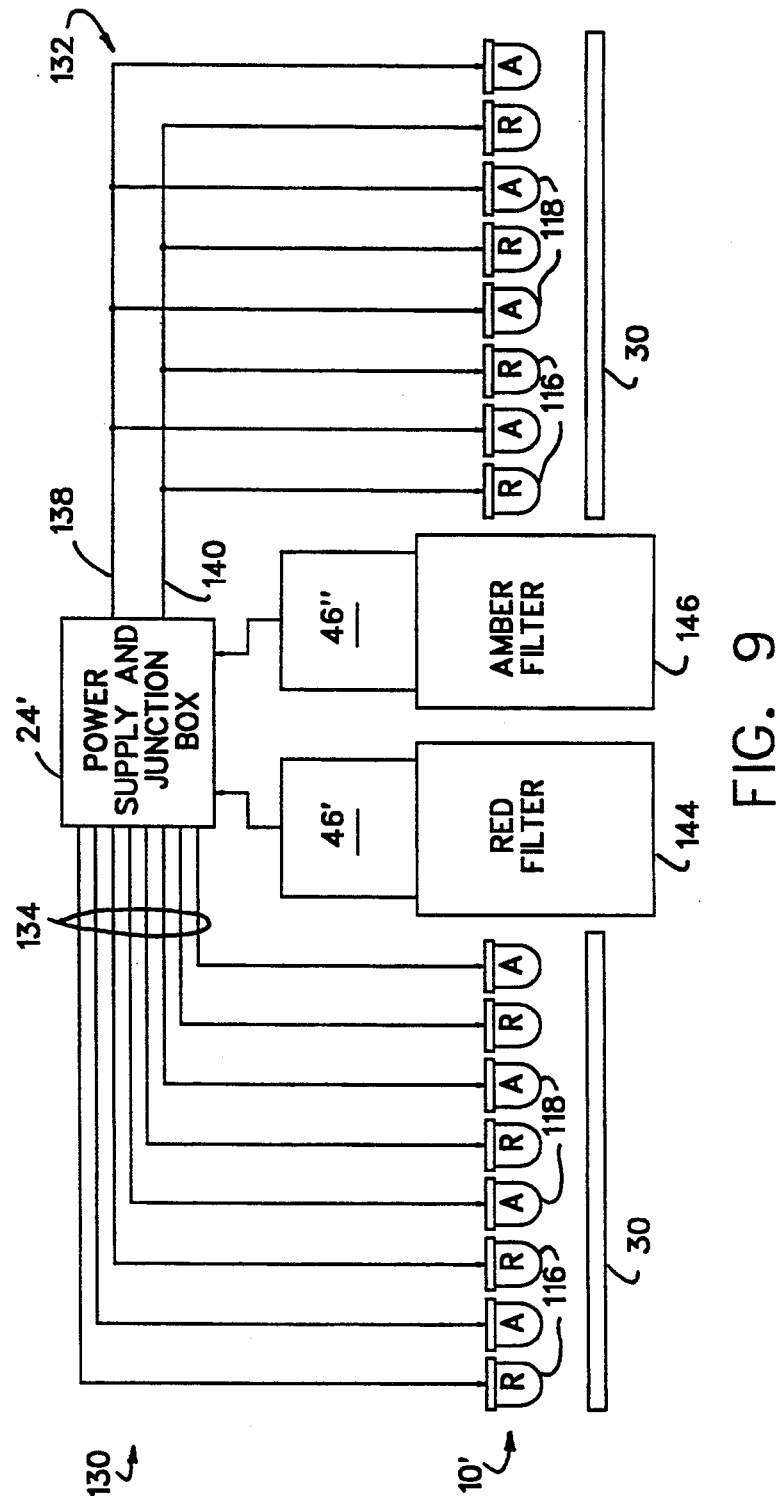

VIDEO INSPECTION SYSTEM EMPLOYING MULTIPLE SPECTRUM LED ILLUMINATION

This application is a continuation-in-part of copending application Ser. No. 658,093, now U.S. Pat. No. 5,172,005 entitled ENGINEERED LIGHTING SYSTEM FOR TDI INSPECTION, filed Feb. 20, 1991.

BACKGROUND OF THE INVENTION

This application pertains to the art of machine vision and more particularly to high speed automated video inspection. The invention is particularly applicable to automated video inspection of continuous web-like materials such as cloth, paper, MYLAR, sheet metal, etc., and will be described with particular reference thereto, although it will be appreciated that the invention has broader applications such as in the inspection of any continuously moving specimen whether discrete or continuous in which the specimen passes through the field of view of an associated inspection camera and in systems utilizing relatively low illumination levels.

Machine vision systems have obtained an established presence in industry to accomplish high speed video inspections. Such machine vision systems are generally comprised of a lighting system to illuminate a specimen and a camera for sensing light reflected therefrom. A digitized image is formed from an image received by the camera. Data representative of this image is then utilized for determining acceptability of the specimen in view of preselected physical characteristics thereof.

Earlier array video inspection systems were typically geared to inspection of a continuous sequence of generally uniform specimens which could be contained within the field of view of the inspecting camera. These systems employed lighting which was sufficient to allow for a single illumination period. Still other earlier systems employed indexed cameras which are progressively incremented relative to a subportion of a large, usually planar, specimen to obtain a series of images thereof.

Substantial product is manufactured as a continuous stream of webbed or sheet-like material. While the aforementioned systems are adequate for a number of inspections, they provide no means for acquiring a consistently detailed inspection image of a continuous stream of fast moving web material. Earlier attempts to achieve automated inspection of such materials relied upon line scan cameras with continuous illumination. Stroboscopic systems were also utilized but required intense illumination periods. It was therefore desirable that a system be provided which allows for detailed high speed video inspection on a continuous stream of web material or which utilizes heretofore inadequate lighting intensities with improved image integrity and which exhibits robustness over a wide range of specimens.

More recently, advances in cameras, and particularly charge coupled device ("CCD") cameras, has led to time delay integration ("TDI"), techniques such as described by U.S. Pat. Nos. 4,922,337 and 4,949,172. TDI employs a CCD array in which rows of CCD elements which are arranged perpendicularly in relation to a direction of propagation of a continuous webbing or other specimens. A continuous light source reflects light from a generally linear cross-section of the specimen to a row of CCD elements. The resultant image data on that row is shifted to a subsequent, parallel row of elements in the CCD array, where additional light flux reflected from the same cross-section of the specimen is integrated therewith. Accordingly, low-light influence due to a single cross-section of the specimen is repeatedly obtained. The resulting combined image averages away substantial noise constituents providing an improved signal-to-noise ratio in a captured image. This allows for obtaining a continuous series of high integrity linear images across the webbing or other specimens.

While the aforementioned TDI technique provides a substantial improvement, it nonetheless presents certain disadvantages. As with more conventional video inspection systems, TDI inspection techniques center on numeric processing, rather than lighting technique. Previous techniques are conducive to some "smearing" of each linear cross-section image. Also, often times different grades of webbing or even entirely different webbing materials may at various times be inspected by the same system. Similarly, non-webbing systems often encounter markedly different specimens at different times. Differences in reflectivity in these situations require compensation. This is typically accomplished by compensation in the inspection algorithm software. Even this is limited given that absolute light sensitivity limits are inherent in CCDs, and once a sensitivity threshold has been exceeded, information is lost and compensation is not possible.

It is also possible to vary lighting intensity, with conventional lighting, however color temperature shifts inherent with incandescent sources and stringent frequency or current controls to effect modification of fluorescent sources are difficult and expensive.

Still more recently, substantial advances have been made in connection with light emitting diode technology. First generation light emitting diodes provided a high portion of their output in the infrared spectrum, which is to be expected from the physical characteristics of the semiconductor substrate from which they were fabricated. Since then, different semiconductor substrates have been utilized to generate light having wavelength frequency that is higher than infrared. Expectedly, first visible LEDs were primarily red in color.

As different substrates were utilized to form different LED colors, another physical property was manifested. It will be recalled that total light energy is related to a frequency by Planck's constant by the equation:

$$E = h\nu$$

While this is of marginal concern in visual displays, where LEDs have and continue to find their dominant application, it is even more critical when LEDs are used for illumination. That is, when frequencies other than red are utilized, the total light energy available for inspection illumination is correspondingly lessened due to the frequency increase.

Further, charge-coupled devices are also fabricated in silicon. Accordingly, their maximum sensitivity is in the infrared area of the spectrum, analogously to the maximum spectral light output of silicon. Accordingly, first generation video illumination, utilizing LEDs, was with infrared lighting. Second generation lighting employed visible red LEDs. Recent advances and LEDs have provided other colors with a usable amount of energy. Further, advances in CCD technology have allowed for increased sensitivity to different illumination spectra.

The present invention contemplates a new and improved TDI video inspection and engineered lighting system which overcomes all the above-referred problems, and others, and provides a video inspection system allowing for continuous inspection of a stream of web materials or other specimens with improved integrity utilizing multiple or selectable color spectra.

SUMMARY OF THE INVENTION

Fundamental to engineered lighting are several factors. These include angle of illumination, intensity of light, purity of light, and light spectrum. These factors may be altered and arranged to achieve lighting for highly application specific situations. Heretofore, systems have failed to seize upon the spectral aspects. Spectral control provides distinct advantages which are augmented when used in combination with the others.

In accordance with the present invention, an engineered lighting video inspection system includes an array of light emitting elements formed of LEDs of multiple spectral characteristics. The light emitting elements of the array are secured such that they are controllable in one or more discrete subsets. A signal representative of a linear velocity of an associated specimen relative to the array is provided to a controller. The controller, in turn, functions to selectively enable the light emitting element for a short time period. Light of the array of light emitting elements is, after exposure to the specimen, communicated to a light sensitive transducer array, the rows of which are synchronized to a continuous webbing material or other specimen.

In accordance with yet another aspect of the present invention, backlighting is provided by a selected plurality of lighting elements disposed on a side of the specimen opposite of the light sensitive transducer.

An advantage of the present invention is the provision of a video inspection system for accomplishing detailed inspection of a continuous stream of sheet or web-like materials or other specimens when the specimens are of varying or various colors.

Another advantage of the present invention is the provision of an inspection system employing selected illumination spectra.

Another advantage of the present invention is the provision of a video inspection system for inspecting a continuous stream of sheet or web-like materials or other specimen using multiple cameras and a concurrent illumination.

Another advantage of the present invention is the provision of a video inspection system for accomplishing detailed inspection of continuous stream of sheet or web-like materials or other specimen while allowing for inspection of flaws which are not discernable by a particular illumination spectrum.

Another advantage of the present invention is the provision of a system which allows for obtaining a frozen image of sequential areas of the web material with the multiple or selective spectral illumination noted above.

Yet another advantage of the present invention is the provision of a system which allows for accumulation of multiple image data sets from selected areas of a continuous stream of web materials to accomplish improved high speed, detailed video inspection thereof with relatively low light levels of multiple or selective spectral illumination as noted above, in a system adaptable to a wide range of webbing materials.

Yet another advantage of the present invention is the provision of an inspection system for improved inspection of discrete images.

Yet another advantage is the provision of an inspection system which achieves an improved signal-to-noise ratio for captured images.

Yet another advantage is the provision of an inspection system employing lighting having improved characteristics, consistency, stability and reliability.

Further advantages will become apparent to one of ordinary skill in the art upon reading and understanding the subject specification.

BRIEF DESCRIPTION OF THE DRAWINGS

The invention may take physical form in certain parts and arrangements of parts, preferred and alternate embodiments of which will be described in detail in the specification and illustrated in the accompanying drawings 30 which form a part hereof and wherein:

FIG. 8 illustrates a multiple, spectrum arrangement of LEDs suitably utilized in conjunction with the subject illumination system;

FIG. 9 illustrates a subportion of the subject inspection system employing different colored LEDs with cameras sensitized thereto;

DETAILED DESCRIPTION OF THE PREFERRED AND ALTERNATE EMBODIMENT

Figure 1:
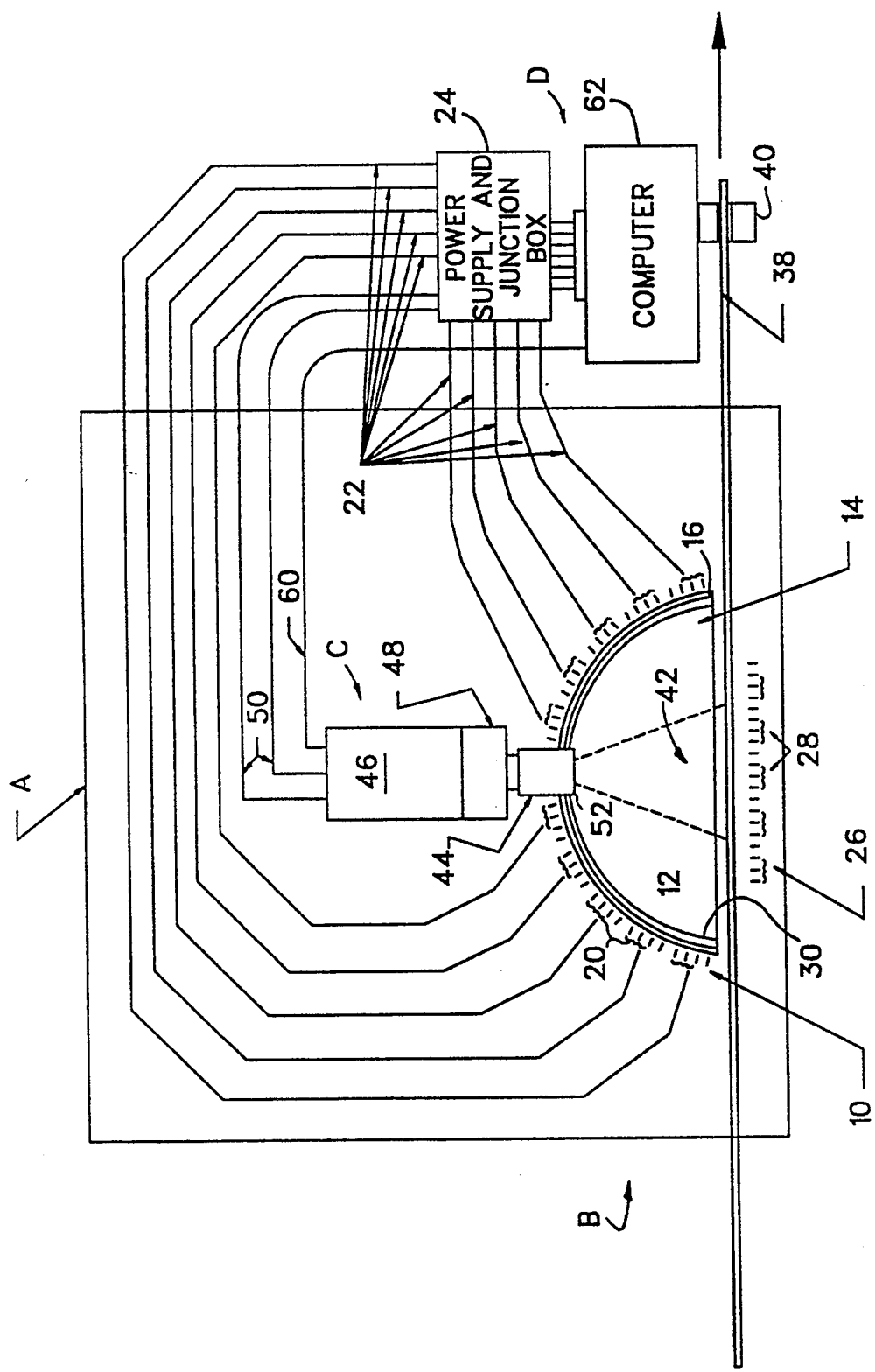
FIG. 1 illustrates a video inspection system employing an array of light emitting diodes.

Referring now to the drawings, wherein the showings are for the purpose of illustrating the preferred and alternate embodiments of the invention only and not for the purposes of limiting the same, FIG. 1 illustrates an engineered video inspection system A which includes an engineered illumination system or means B, a data acquisition system or means C, and a computer system or means D.

The illumination system B is formed from an array of a plurality of light emitting elements 10 preferably comprised of solid-state lighting elements, such as a plurality of light emitting diodes ("LEDs"). Light emitting diodes advantageously provide a fast responsive, long lived, and consistent light output.

Present solid-state light generating elements are available in colors ranging from infrared to blue. Each has distinct advantages for illumination. Selection of wavelength or wavelengths of light vary in conjunction with the selected inspection. Additional consideration is merited by the proportion of illumination energy to the color of light as dictated by $E=h\nu$, where $E$=energy, $\nu$=frequency of light, and $h\nu$=Planck's constant. Earlier LED inspection systems typically employed infrared or red elements given this frequency/energy relationship and the necessity of providing large quantities of light to overcome a short exposure time. Steady-state lighting TDI integrated over a period of time inspections require substantially less light per illumination, thereby rendering possible illumination by various frequency combinations. Repeated, integrated, lighting exposure/image capture sequences allow for use of green, or even blue LEDs notwithstanding their lower efficiency of output. Also, mixed spectra are advantageously implemented to specific inspections. Influences due to multiple light frequencies provide three-dimensional information, as well as a means by which various colors of specimens are inspectable. Multiple cameras are suitably implemented with sensitivity to selected spectrum to isolate various spectral influences or anomalies which are suitably illuminated with one spectrum and another with a second or a third. Selected charge-coupled-device ("CCD"), arrays, filters or splitters are suitably implemented to accomplish this.

In the preferred embodiment, the light emitting diodes are focused to a generally narrow beam or cone of light emanating therefrom, which cone has a generally selected angle. However, a similar effect to a focused LEDs may be realized by employing a wider beam coupled with a decreased distance between the LEDs and a specimen.

Typical, focused, light emitting diodes include a bullet-shaped casing which functions as a lens to project the narrow beam or cone of light therefrom. What focus is used, the arrangement of the devices, and the angles of illumination chosen is extremely application dependent. Conventionally available focused light emitting diodes have a beam of light generally wide angle (20° at the vertex), or 10° from a perpendicular centerline thereof. The subject system employs selection of LED angles which are highly application dependent. The more focused LEDs allow for concentration of a maximum amount of light from a given LED in a small area while concurrently maintaining uniformity in illumination. This also provides for a higher intensity of illumination on a specified area, subjecting the area to individual controllability of intensities and angles thereacross to controllability of individual or groups or subsets of light emitting diodes.

Light emitting diodes may be pulsed at extremely high currents provided that the duration is sufficiently small to prevent heat build-up which may damage the PN junction forming the diode. It is found that a duration in the range of 1 to 200 microseconds allows for provisions of such high currents with no or nominal damage to the LED. As will be described further below, it will be seen that this duration is also sufficient to "freeze" the image of a rapidly moving specimen so that a still image may be captured therefrom. In the preferred embodiment, 240 scan lines are implemented in the CCD array. Accordingly, 240 pulses and 240 exposures are integrated for each linear cross section of a specimen.

The subject system concurrently flashes all or some of the diodes 10 in a duration of approximately 4 $\mu$sec given the light accumulation properties of TDI. However, operation in the range of 0.1 $\mu$sec to 100 $\mu$sec returns most advantages associated with the subject system. Each LED is suitably supplied with between 1 mA and 500 Ma of current during this duration. A value of 73 mA has proven acceptable. Suitable power supplies to accomplish such pulsing are well within the understanding of one of ordinary skill in the art and will not be described herein. The 4 $\mu$sec time is selected to advantageously provide low duty cycle compared to the typical horizontal scan time for NTSC video signals. A 15.75 Khz scan rate provides a 63 $\mu$sec horizontal scan time. Accordingly, the 4 $\mu$sec pulse provides a 4/63 duty cycle. This particular rate with actual duty cycle is proportioned to a scan rate implemented for a particular application.

In the embodiment of FIG. 1, the light emitting diodes 10 are secured by a bracket or securing means 12 in a generally hemi-cylindrical array 16. Such an array structure advantageously provides generally uniform illumination to a rectangular light field 14. This structure is suitably fabricated from a flexible printed circuit board portion secured to two hemispherical printed circuit board end portions. LEDs are mounted on the interior portion of the array 16, and are preferably placed as closely as possible to one another to maximize illumination and minimize transitions therebetween, thereby forming a more uniform light field. Although this particular structure is employed in the preferred embodiment, it will be appreciated that various other array structures may be employed for illumination of various specimens.

Angled lighting, i.e., lighting which communicated from one or more LEDS to a specimen and is reflected off the specimen surface to a camera with a stated angle at less than 180°, is advantageously employed for improved detection of certain surface defects. Such systems may optionally implement a perspective correcting lens to maintain image characteristics through the progression within the CCD array. Such a perspective correcting lens allows for direction of light from an array to a specimen at a non-perpendicular angle while negating artifacts which would otherwise result from such an orientation. For example, angled (non-perpendicular) light from a rectangular array which illuminates a specimen causes a trapezoidal illumination area. Moreover, the video receptor of the resultant image is similarly distorted. The reflected image of the lens itself can thus be eliminated by use of a perspective correcting lens when highly reflective materials are being inspected thus allowing the desired degree of homogeneity in the imaged web.

The light emitting diodes 10 are also suitably subdivided into a plurality of groups or subsets 20. Light emitting diodes of each of the subsets 20 are controlled together via connections 22 with a power supply and junction box 24. Grouping of the light emitting elements provides a means with which control of the intensity along selected subsections of an associated specimen may be made or by which selected angles of illumination may be provided. Such structure also provides an ability to compensate for degrading or burned-out elements by boosting output of surrounding elements. It further provides for reduction of reflected light reaching any given region of the camera sensor.

A illustrated in FIG. 1, a portion of the light emitting elements 10 is formed into a backlight array 26. Backlighting is often advantageously employed for inspection of light transmissive specimens or subportions of specimens. In the illustrated embodiment, the backlight array 26 is secured so as to be generally planar. Such a planar orientation is generally best suited for backlighting applications, although it will be appreciated that various other orientations may be successfully utilized. As with lights of the primary array portion 16, light emitting diodes of the backlight array 26 are suitably formed into a plurality of subsets 28, interconnected with power supply and junction box 24. These connections have been omitted from FIG. 1 for ease in illustration. Such formation of subsets provides for controllability analogous to that provided with the arrangement above-described for primary array portion 16.

Illustrated in FIG. 1 is a cross-sectional side view of a diffuser 30. The diffuser 30 is advantageously formed as a hemi-cylindrical shape to be similar to the shape of the array 16, and placed internally thereof. The optional diffuser functions to smooth transitions between LEDs of the array, thereby providing an even more uniform light field.

Also illustrated in FIG. 1 is segment 38 of a stream of webbing material which is in generally continuous motion in the direction so indicated. Again, as used herein, webbing material will be understood to refer to any sheet-like material, such as paper, cloth, sheet metal, plastic, laminates, and the like. It is understood that the system is also advantageously employed in discrete specimen systems. However, for simplicity descriptions herein will generally be with sole reference to webbing environments. A conveyor driver (not shown) continuously moves the web 38 through the light field 14 at a generally high speed. Web position is measured by a web position/velocity sensor, such as a tachometer 40. Light from light emitting diodes 10 of the primary array portion 16 is reflected from the web 38. Reflected light from a viewing area 42 is received through a lens 44 of a camera 46. Although only one camera is illustrated in the cross-sectional view of the figure, it will be shown below that often a plurality of cameras are advantageously employed. The viewing area 42 is isolated as much as possible from ambient light, i.e., light not provided by light from the primary (or secondary) lighting array(s) 16 (28).

In the embodiment of FIG. 1, the lens 44 of camera 46 is secured to extend slightly into the light field 14 through an aperture portion 52. The lens 44 is preferably formed as a "pinhole" unit to minimize image artifacts due to the camera itself. Such lens arrangements are typically less than ⅜" in diameter. In a symmetrical array such as the hemi-cylindrical primary array portion 16, the aperture portion is suitably disposed at a generally central portion of the array should one camera be utilized, and at equivalent intervals in embodiments employing a plurality of cameras. The subject system, in its preferred embodiment, employs a TDI camera, VISIONEER 4050 manufactured by Picker International, Inc.

The camera 46 includes a CCD array in the preferred embodiment. It will be appreciated that CCD arrays are usually M×N rectangular arrays of photosensitive transducer elements, wherein M and N are positive, non-zero integers, usually multiples of two. The camera of the preferred embodiment functions as 244 rows of CCD elements, each row having 610 pixels.

In the arrangement of FIG. 1, the camera 46 is oriented relative to the web 40 such that each row is generally perpendicular to the direction of travel thereof. Typical CCD arrays are sensitive to a selected number of gray scale levels, for black and white systems, or primary colors, for color systems.

Commonly available CCD cameras allow for individual addressing of rows of transducer element thereof, analogously to the raster scan associated with conventional cathode ray tubes ("CRTs"). CCD elements also operate as integrators which provide an electrical signal representative of an intensity of light exposed thereto over time. A CCD transducer element also has the ability to store light intensity data. This property is useful for achieving a still image of a specimen or portion thereof by strobing or pulsing a light source when the moving specimen is otherwise in a generally darkened field of view.

The camera 46 also advantageously includes an adjustment system 48 for control of focus, planetary, vertical, horizontal properties. Orthogonality must be maintained between sensor and inspected material. Such adjustment may be done manually, or in conjunction with signals provided by the digital computer system D by data communication camera sync and control lines.

Image data acquired from camera 46 is communicated, through video signal line 60, to the digital computer system D, and more particularly to the computer 62 thereof. The computer 62 includes a central processor (CPU), memory, an I/O unit, and a suitable software and junction box 24 and with the webbing speed sensor 40. The computer 62 determine acceptability of the specimens by a comparison of digitized image data with data representative of acceptability.

Figure 2:
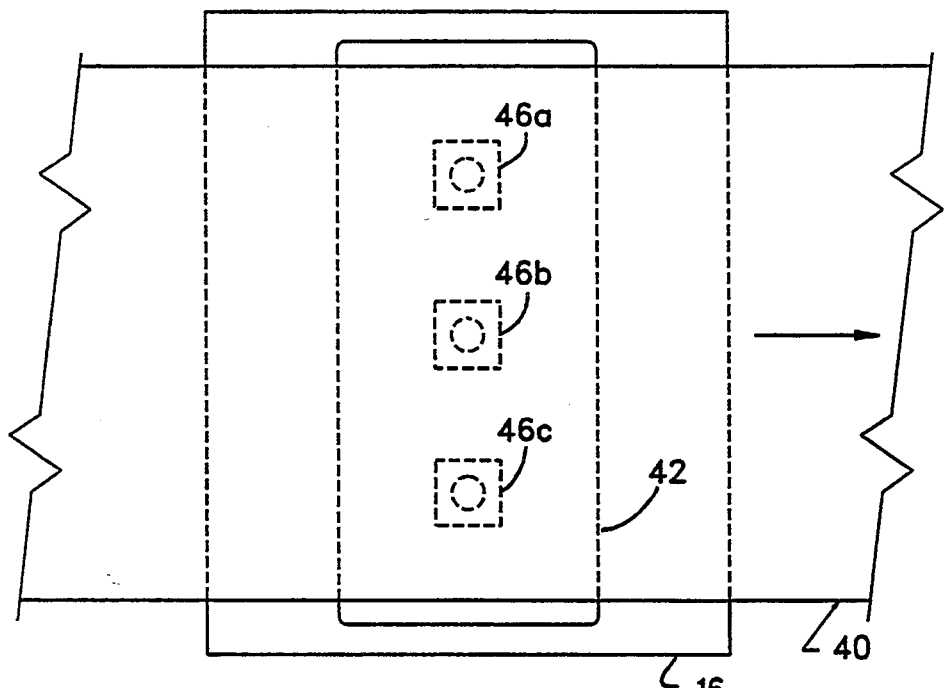
FIG. 2 illustrates an overhead view of three cameras positioned to accomplish image acquisition for inspection of webbing material.

Although only one camera is visible in the embodiment of FIG. 1, certain applications are advantageously served by a plurality of cameras. FIG. 2 illustrates an embodiment in which three cameras, 46a, 46b, and 46c are oriented relative to webbing material 38 in a mutual linear relationship. Respective viewing areas of the cameras are linearly aligned to provided a cross-section of the entire specimen surface. Securing the cameras in this manner provides an extended viewing area 42 sufficient to encompass a cross-section of a relatively wide webbing.

Figure 3:
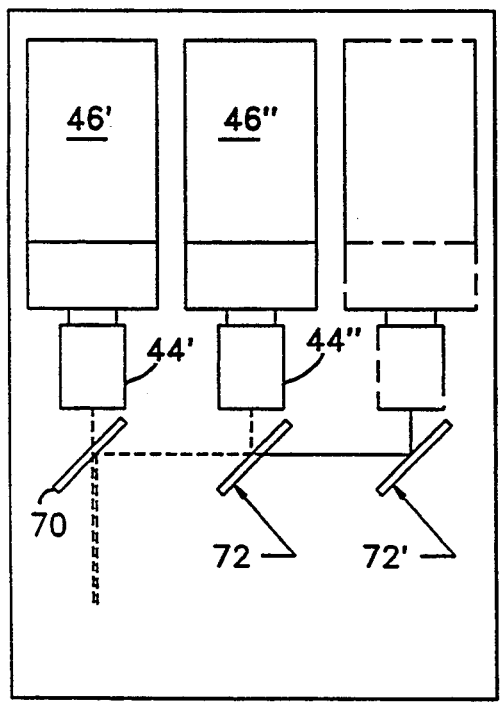
FIG. 3 illustrates an optional dual-camera inspection embodiment.

FIG. 3 illustrates an embodiment in which camera 46 is itself formed from a plurality of cameras. In this embodiment, light from a specimen is communicated to a partially silvered mirror 70. A portion passes directly to lens 44' of camera 46'. A second light portion is reflected from mirror 72 to lens 44" of camera 46". Implementation of a dual or multiple camera structure, such as that illustrated by FIG. 3, advantageously provides a means by which selected portions of the specimen may be provided with either increased resolution to accomplish specialized inspections or optical filtering thereon. For example, a seam or scoring in the inspected web material might be subject to heightened scrutiny by virtue of utilization of a secondary camera element focused specifically thereon. Similarly, a third camera is also advantageously implemented for additional subportion analysis, as illustrated in phantom as numeral 72' in FIG. 3. Lighting to each camera of such multiple camera beam-splitter environments will generally not yield as desirable a result or design because of the intense lighting required to provide enough light to each camera (when the exposure time is short and) since the splitting reduces the intensity inherently.

It will be appreciated that certain application may employ multiple two-camera or three-camera modules, for example, disposed as illustrated by FIG. 2 with suitable magnification and clock speeds.

Figure 4:
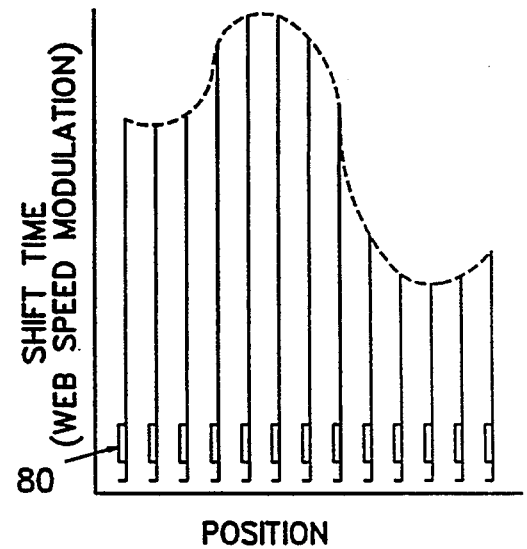
FIG. 4 is a graph of shift time versus position for an inspection of a continuous moving stream of webbing material.
Figure 5:
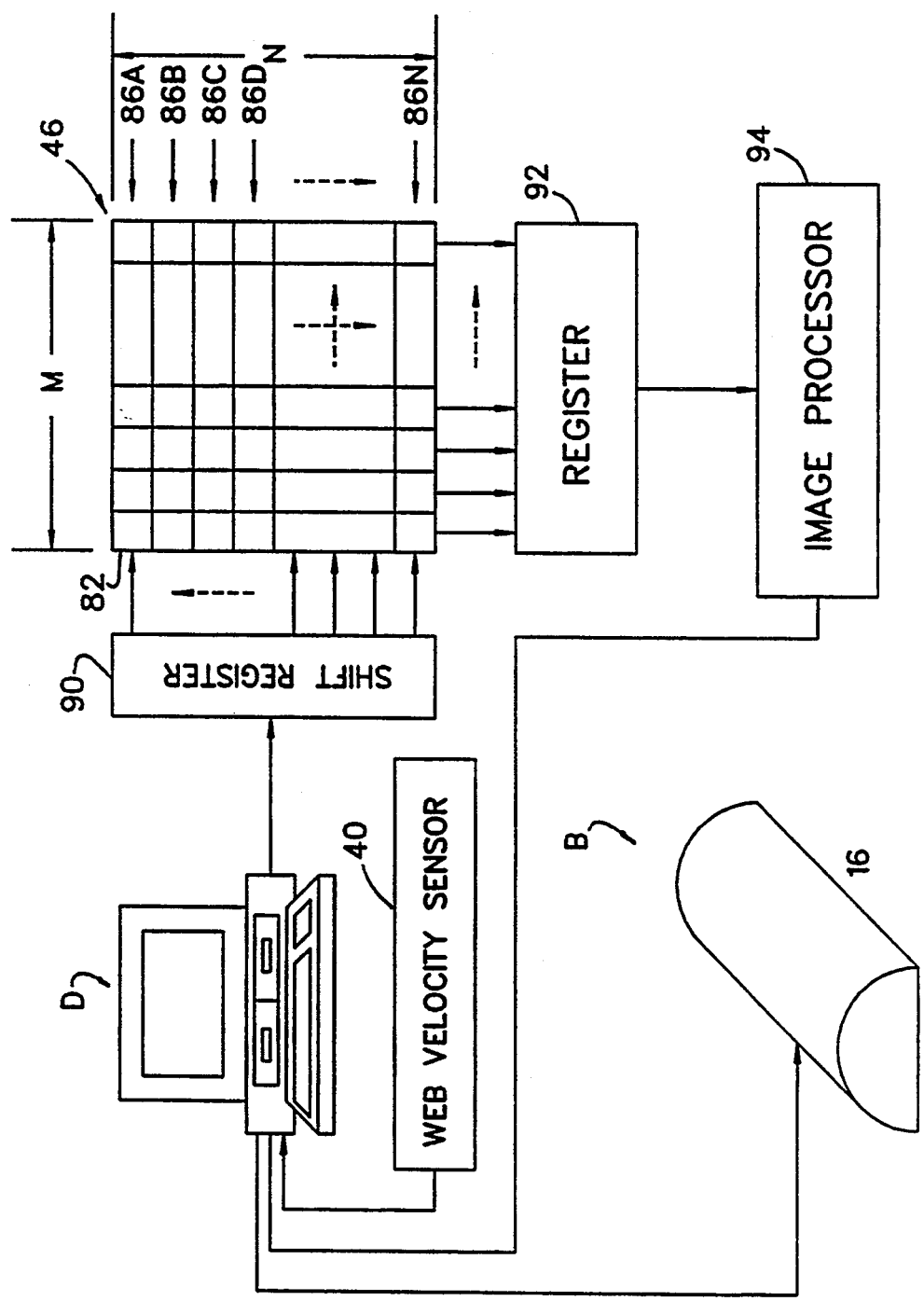
FIG. 5 illustrates the illumination and CCD subsystems employed in the system of FIG. 1.

Turning now to FIGS. 4 and 5, a graph illustrating operation of the charge coupled devices within the camera or cameras 46 is provided. In the illustrated graph, position is represented by the abscissa while shift time is represented by the ordinate. It will be recalled from the discussion above concerning CCDs that light sensitive transducers elements thereof are arranged in an M×N grid. Data in each row of CCD elements is typically sequentially accessed and read in a raster-type fashion. This property is seized upon to accomplish a sequence of linear scans from a plurality of linear cross-sections of the webbing specimen surface. Accessing of scan lines of the CCD array is advantageously synchronized with the velocity of webbing material 38. When non-continuous lighting is chosen, a series of illuminations or light pulses are represented by the rectangles 80 of the graph. In the event multiple cameras are used, rows or scan lines of each are preferably synchronized between all cameras. It is also equivalent to provide multiple pulses per scan line if advantageous.

Synchronization between the CCD and the webbing may be accomplished by control of web velocity or of CCD row increments. In the preferred embodiment, the CCD row incrementing is altered in accordance with variations in web speed by variations in shift control as described below.

With particular reference to FIG. 5, orientation of a CCD array 82 is provided. The digital computer system D, which is illustrated with a keyboard, CRT, and mass storage media, and which includes the computer 62, receives a signal representative of web velocity from a sensor 40. This information is in turn utilized to sequence the scan of row 86 of a CCD array elements 88, via row scan selected circuitry illustrated as shift register 90. Similar sequencing is provided for each CCD array in multiple camera embodiments. The webbing progression is continuously monitored and the shift time implemented by the row select circuitry 90 is altered in accordance therewith. The graph of FIG. 4 illustrates the variation and shift time in accordance with the web speed.

Figure 6:
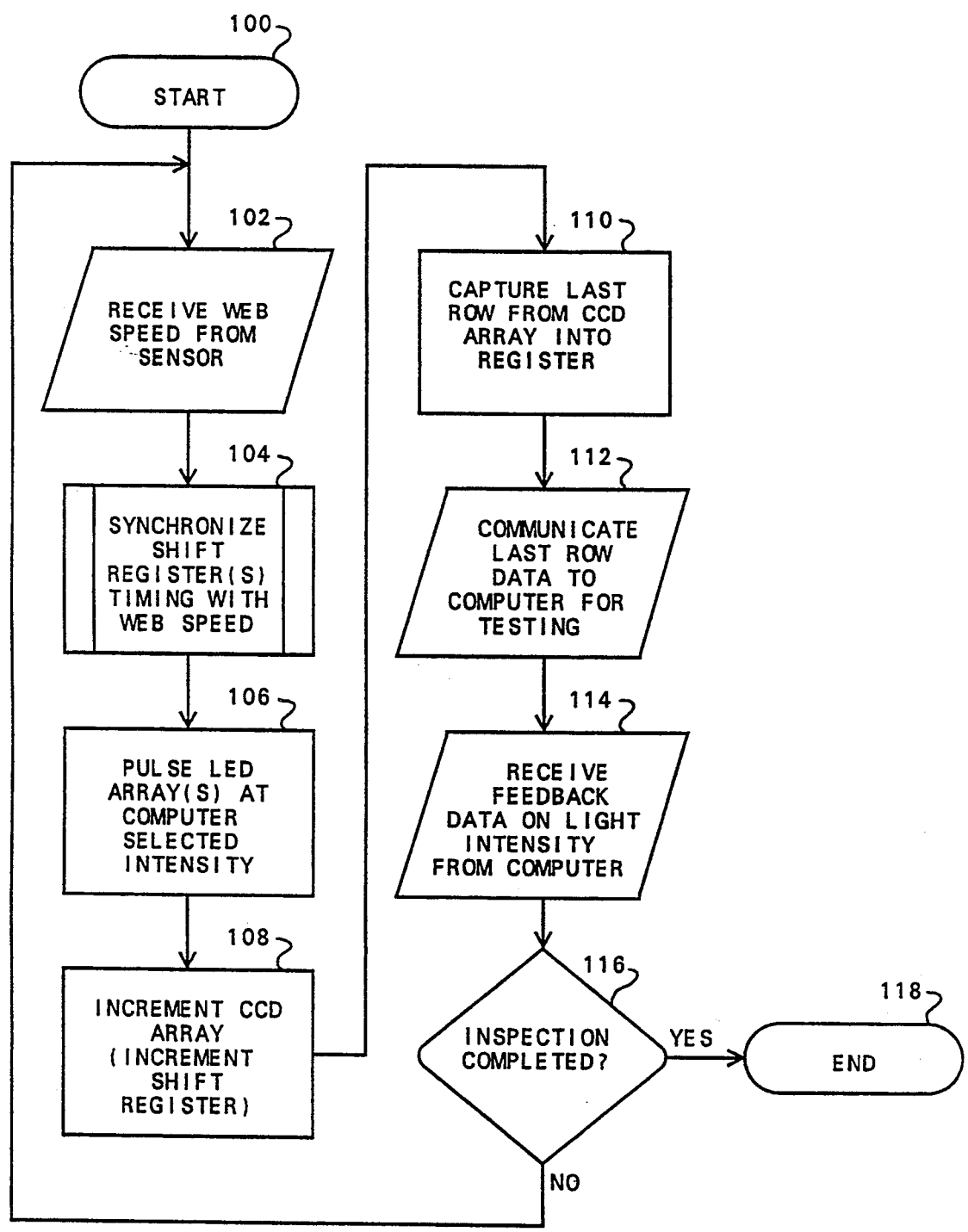
FIG. 6 illustrates a flow chart of operation of the subject TDI engineered lighting inspection operation.

Turning now to FIG. 6, a flow chart illustrating operation of the subject TDI illumination process will be described. The operation commences at start step 100 and progresses to I/O step 102. At step 102, data representative of web speed is obtained from tachometer 40. In step 104, web speed data is utilized to synchronize the shift register or registers of the CCD cameras with the web speed velocity data obtained in step 102. In step 106, the array or arrays of LEDs is pulsed for a short duration, approximately 4 μsec. in the preferred embodiment as noted above. This duration, by virtue of the synchronization with the webbing speed, is timed at the point when the previous shifting operation has settled, thereby providing the minimized smearing. Lighting intensity is also alterable in connection with this step.

At step 108, the digital computer instructs shifting of shift register 90 to cause progression of rows of the CCD array 82 towards register 92. Accordingly, at this time the contents of previous row 86N are then communicated to register 92 in step 110. This data is, in turn, communicated through image processor 94 to digital computer system D at step 112. At this stage, a suitable algorithm is performed on the data to determine acceptability of the specimen.

At step 114, lighting intensity adjustment data is received to allow for selective control of intensity in step 106. Step 116 allows completed inspections to terminate at step 118 and continuing inspections to progress back to step 102.

Figure 7:
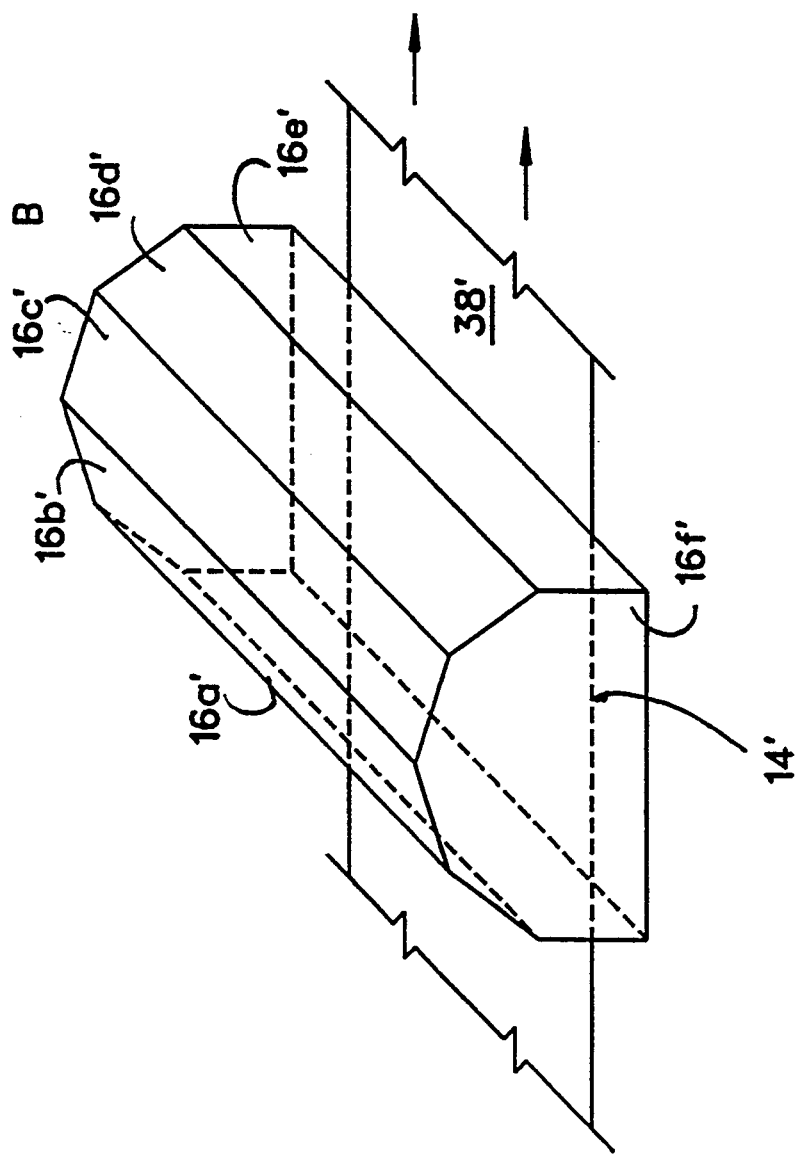
FIG. 7 is an alternate embodiment of the primary lighting array illustrated in FIGS. 1 and 5.

FIG. 7 illustrates an alternative embodiment of the primary array 16 illustrated in FIGS. 1 and 5. In this embodiment, the primary array 16' is formed from a series of planar rectangular portions 16a'-16d' and first and second planar end portions 16e' and 16f'. As with the hemi-cylindrical array illustrated in FIGS. 1 and 5, an interior portion of the array 16' contains closely packed LEDs directed to the webbing material 38'. This embodiment advantageously allows for fabrication of the array 16' from common, planar printed circuit board material. This orientation nonetheless provides for substantial uniform illumination over a light field 14' which encompasses a portion of the webbing 38'. It will be appreciated that more or fewer rectangular subsections may be utilized depending on the degree to which a hemispherical array is more closely advantageously approximated. Further array formats may also be utilized, which formats are dictated by properties or dimensions of the webbing material and the angles and intensities of illumination required to provide the desired qualities of the illumination. For example, hemispherical, "tiffany-lamp" style, etc. may be utilized.

The modulated row select CCD structure provides a system with which multiple readings of a single linear subsection of a continuously moving web material may be achieved without the necessity of using a plurality of cameras or a moving camera. Data achieved by multiple acquisition provides more reliable data upon which inspection may be made. Also lighting specific to subsections of the CCD may be advantageously applied at appropriate angles and intensities.

Turning it now to FIG. 8 with added reference to FIG. 1, an embodiment is described wherein multiple spectra illumination is achieved. Therein, a plurality of illumination quanta are obtained by implementation of a plurality of LEDs 116 having a first specified wavelength range and a plurality of LEDs 118 having a generally second wavelength range, distinct from the first wavelength, The LEDs 116, 188 of array 10' are provided for illustration. It is to be understood that the array 10' provides an alternative embodiment to a single-color array, suitable for implementation in connection with the engineered video inspection system A and more particularly in connection with the array 20 or backlighting array 28.

The arrangement of LEDs 116 and 118 of the embodiment of array 10' of FIG. 8 provide both red and amber spectra. Presently, amber LEDs are available which will generate light output in the range of 700-900 millicandella/watt. While the utility and advantages, to be noted further below, from multi-spectra are achievable with any combination of LEDs, the combination of red and amber is particularly suited to inspections in connection with conventional, present-day LED and CCD components. As noted above, significant light output from red LEDs, particularly when provided with high current for a short duration, has been available in the past. More recently, the spectrum of relatively high output LEDs has progressed to the wavelengths of orange light through to amber while retaining a significant light energy output. The amber color, selected for the second component wavelength, balances both relatively high energy output with significant distance from red to achieve utility as will be appreciated below.

The arrangement illustrated by FIG. 8 provides a compact physical array arrangement achieved by staggering LEDs, as evidenced between rows 122 and 124, such that a perimeter of an LED from row 24 extends into an area between perimeters of adjacent LEDs of row 22, and vice versa. This compact ordering allows for maximum light output per unit area of an array surface.

The structure of the array 10' is further illustrated as comprising equal numbers of red LEDs 116 and amber LEDs 118. As color selection for a particular, multichromatic inspection is highly application dependent, so are relative intensities between spectra. That is, compensation between relative spectra intensities is suitably adjusted by varying a proportion of one spectra relative to one, or more other spectra provided by LEDs of the array to provide a base illumination. Of course, the base illumination is alterable by selective LED enablement as well as by varying current drive levels or "on" duration. It might be expected that LEDs have a significantly lower output or if camera sensitivity to the amber light would be lessened thereto. This is suitably addressed with a proportionally greater number of amber LEDs to red LEDs, application of a higher current to the amber LEDs, or increased "on" time of the amber LEDs, alone or in combination to balance this difference.

While monochromatic light, such as the red light utilized from earlier LED-based video inspection illumination systems, performs admirably, certain advantages are nonetheless to be gained by implementation of multiple chroma. First, is desirable to have an inspection system which may obtain usable video inspection of a variety of specimens. However, this requires an inspection system versatile enough to inspect specimens of various, or varying colors. However, specimen color may render inspection via illumination from a particular frequency to be of limited or no value. Further, an alternative light frequency might itself suffer when used in connection with other specimens. The subject invention satisfies this problem by providing a system which allows for selective illumination by multiple light frequencies.

In addition to the foregoing, multiple frequency inspection illumination provide an ability to realize additional advantages. That is, certain specimen characteristic render illumination and inspection of an entire specimen, at one time, difficult or impossible. For example, inspection of a concave specimen may require unique lighting, due to angle, orientation, disposition, or color, relative to another portion. Traditionally, such inspections were completed with multiple passes before plural inspection stations, or with repeated passes on a single inspection station.

Multiple pass inspection systems suffer from several drawbacks. First, additional hardware is necessary to build redundant or duplicative inspection stations. Multiple inspections through a single system provide additional materials handling and add to the total inspection time. Further, results from each of the multiple inspections must be integrated with their correct counterpart to accurately determine specimen acceptability. Thus, additional information handling, communication, and processing is required. This, of course, adds to structural and computing costs. Finally, inspection system must often be integrated into product manufacturing lines already in existence. Accordingly, the amount of line space which may readily be adapted to addition of heretofore unutilized video inspection may be limited.

Turning now to FIG. 9, illustrated is a portion of the array 10', together with a sufficient segment of the video inspection system A and computer system or means D to illustrate the particulars of a modified embodiment to that described hereinabove. Also illustrated is a portion of the diffuser 30 and a modified power supply and junction box 24'. Also illustrated in FIG. 9 are two alternative interconnections between LEDs of the array 10' and the power supply and junction box 24'. The ground or common connection to each LED is not illustrated for ease in viewing. Either or both interconnections, as illustrated by portions 130 and 132 are suitably implemented. The portion 130 is a direct LED control for individual, or small subgroups, of LEDs as dictated by power supply and junction box 24'. The portion 132 illustrates a banked LED control. The portion 130 provide a unique control line of a grouping 134 to each LED or subgroup of LEDs. In the banked LED control of the illustration, the group, or subgroup, of red or amber LEDs are controller via a single line 138 or line 140, respectively. The illustrated interconnection of the direct LED control portion 130 advantageously allows for customizable lighting, both to lighting location, intensity, and spectrum. However, a trade-off is provided by control complexity, as well as control line complexity as illustrated by control lines 134.

The LED bank control 132, conversely, maintains relatively simplified control and wiring. However, it suffers from the spatial, spectral, and intensity flexibility of the portion 130 by requiring control of a single color. Of course, it will be appreciated that multiple LEDs may also be utilized in a single, array-wide control such that the entire array is pulsed or strobed with a single, uniform multi-chromatic light pulse.

A specimen so illuminated by the multi-chromatic light will result in reflected (for frontal lighting) or transmitted (for backlighting) light of one or plural spectra. Such light is received in the embodiment of FIGURE 9 in first and second video receptors illustrated as cameras 46' and 46". In the preferred embodiment, these cameras are similar to those of camera 46, noted above. However, the camera 46' has affixed thereto a first filter 144 adapted to filter a selected wavelength, illustrated as red. The filter 144 intercepts light after reflection from the specimen prior to exposure of the camera 46'. Accordingly, the camera 46' would primarily be sensitive to the inspection areas which are revealed by the amber light from the LEDs 118 by virtue of filtering of the red light prior to exposure of the camera light sensitive element.

As with camera 46', camera 46" has affixed thereto an amber filter 146. As with the camera 46', flaws discernable by illumination of the LED 118 would be discernable from the camera 46" by virtue of filtration of the amber spectrum prior to exposure.

Again, although amber and red have been illustrated in the preferred embodiment, it will be appreciated that various combination are of two or more LEDs are suitably implemented in this embodiment, provided that a suitable number of corresponding camera/filter combinations are provided therewith. It must be emphasized that such choices of light spectrum and illumination are highly application specific.

Figure 10:
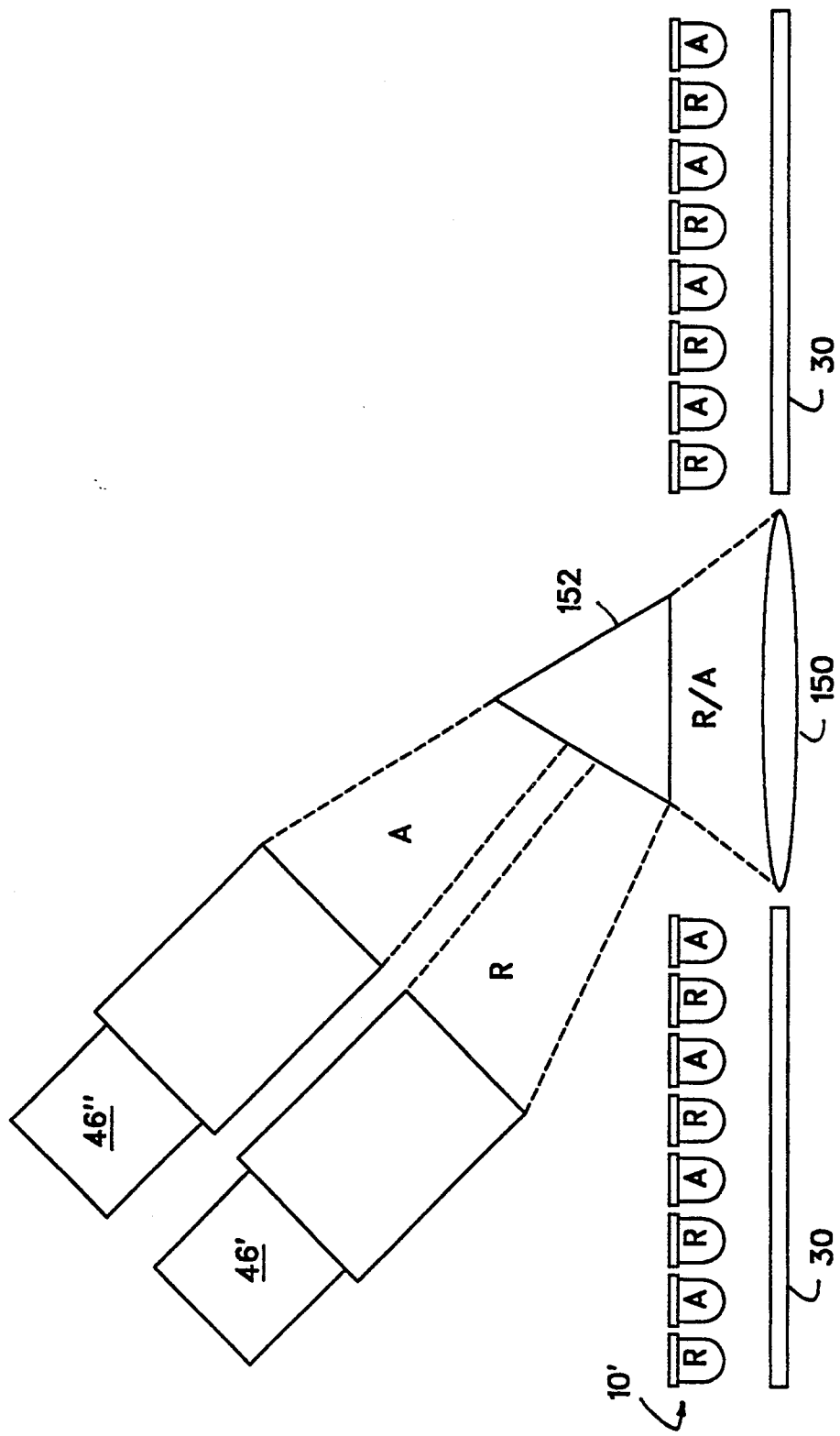
FIG. 10 illustrates an embodiment employing a lens and prism system illustrating both individual and grouped element control.

Turning now to FIG. 10, a modified portion of the structure of FIG. 10 is provided. Specific interconnection for control of the LEDs 10' will be understood to be similar to that described in connection with FIG. 9. While the embodiment of FIG. 9 employed filters, spectral separation in the embodiment of FIG. 10 is accomplished by virtue a lens 150 and a prism 152. The lens 150 serves to gather light resultant from exposure to a specimen and communicating it to the prism 152. As will be appreciated, prism 152 functions to provide spatial separation of polychromatic light which is a well known prism property. An advantage associated with prism usage is that since spectral separation is accomplished by relative indices of refraction, lessened intensity loss relative to that expected from a filter is obtained.

Figure 11:
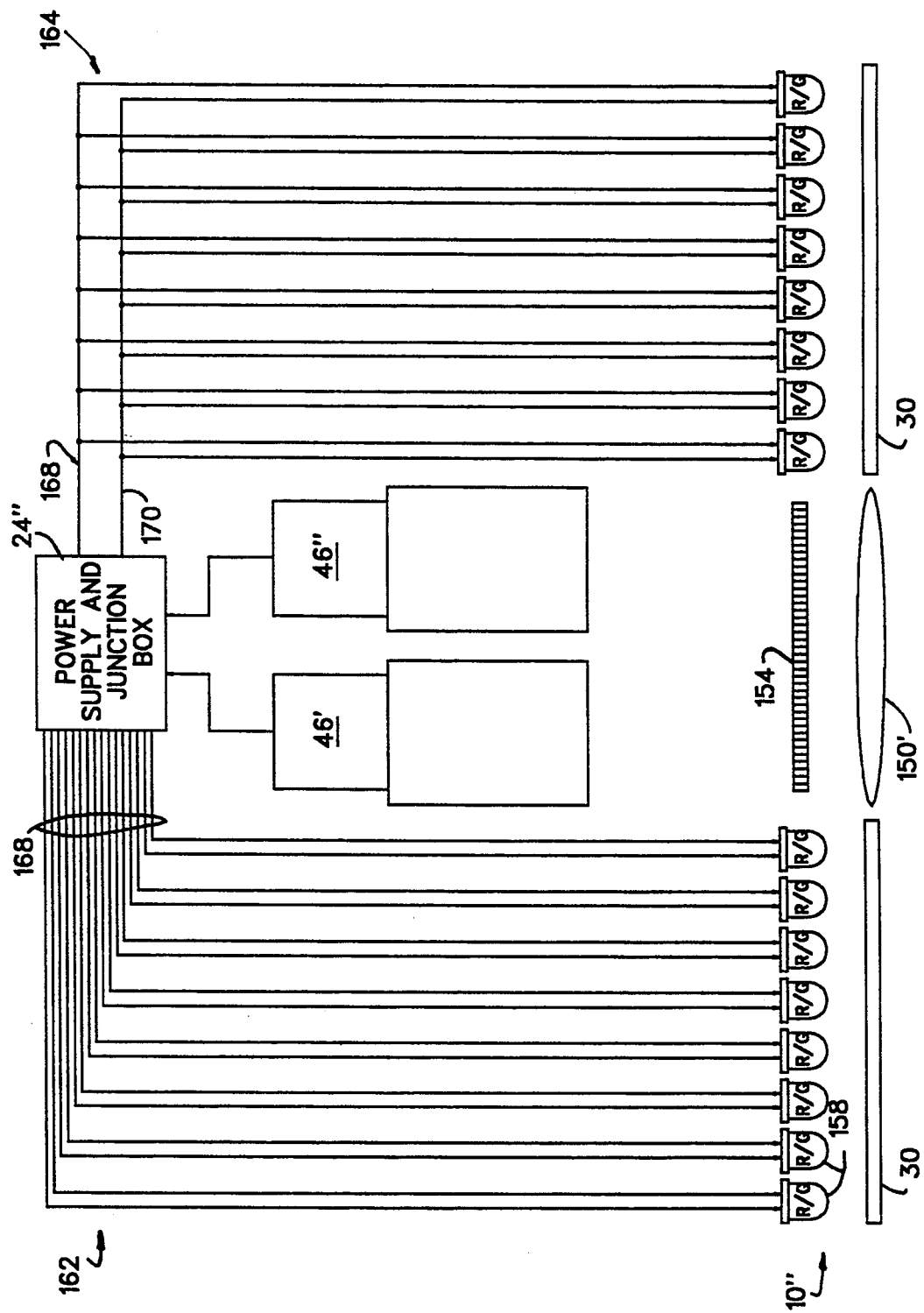
FIG. 11 illustrates an embodiment employing a diffraction grating and multi-color LEDs illustrating both individual and grouped element control.

Turning now to FIG. 11, yet another embodiment illustrating several, alternative structures is provided. First, a combination of a lens 150' and a diffraction grating 154 is utilized for spectral separation. It will be appreciated that a diffraction grating, such as at 154, utilizes diffractive properties of light through a slit system to accomplish spectral separation analogously to the prism 152 of FIG. 10. As with FIG. 10, first and second cameras 46' and 46" are spatially separated in accordance with spectral displacement resultant from the grating 154.

Also illustrated in FIG. 11 is an array 10" of LEDs. LEDs 158 of the array 10" are each multi-spectral. Presently, LEDs which are capable of providing multiple colors are available. Typically, a first signal to the LED dictates are first color while a second signal to the LED dictates the second. As with FIG. 9, two interconnections between a further modified power supply and junction box 24" and a first LED portion 162 and a second LED portion 164 are illustrated. Again, either or both of such interconnections are suitably implemented.

The first portion 162 provides two interconnections between each LED thereof and the power supply and junction box 24". In this way, various LEDs 158 of the array may be activated, selectively by position and/or color. As with the portion 134 of FIG. 9, a trade off is provided in the complexity resultant to the power supply and junction box 24", as well as complexity of interconnection via connectors 168.

Also, the second portion 164 provides banked control analogously to the bank control of portion 132 of FIG. 9. A line 168 suitably provides banked control of a first color of each LED, illustrated as green. Similarly, line 170 provides bank control of the second color associated with each LED, red in the illustration. Although the illustration of the composite LEDs of FIG. 11 is provided with a lens/diffraction grating arrangement, it will be appreciated that the filter approach, the prism approach, and the diffraction grating approach may be interchanged between the various depictions thereof.

Figure 12:
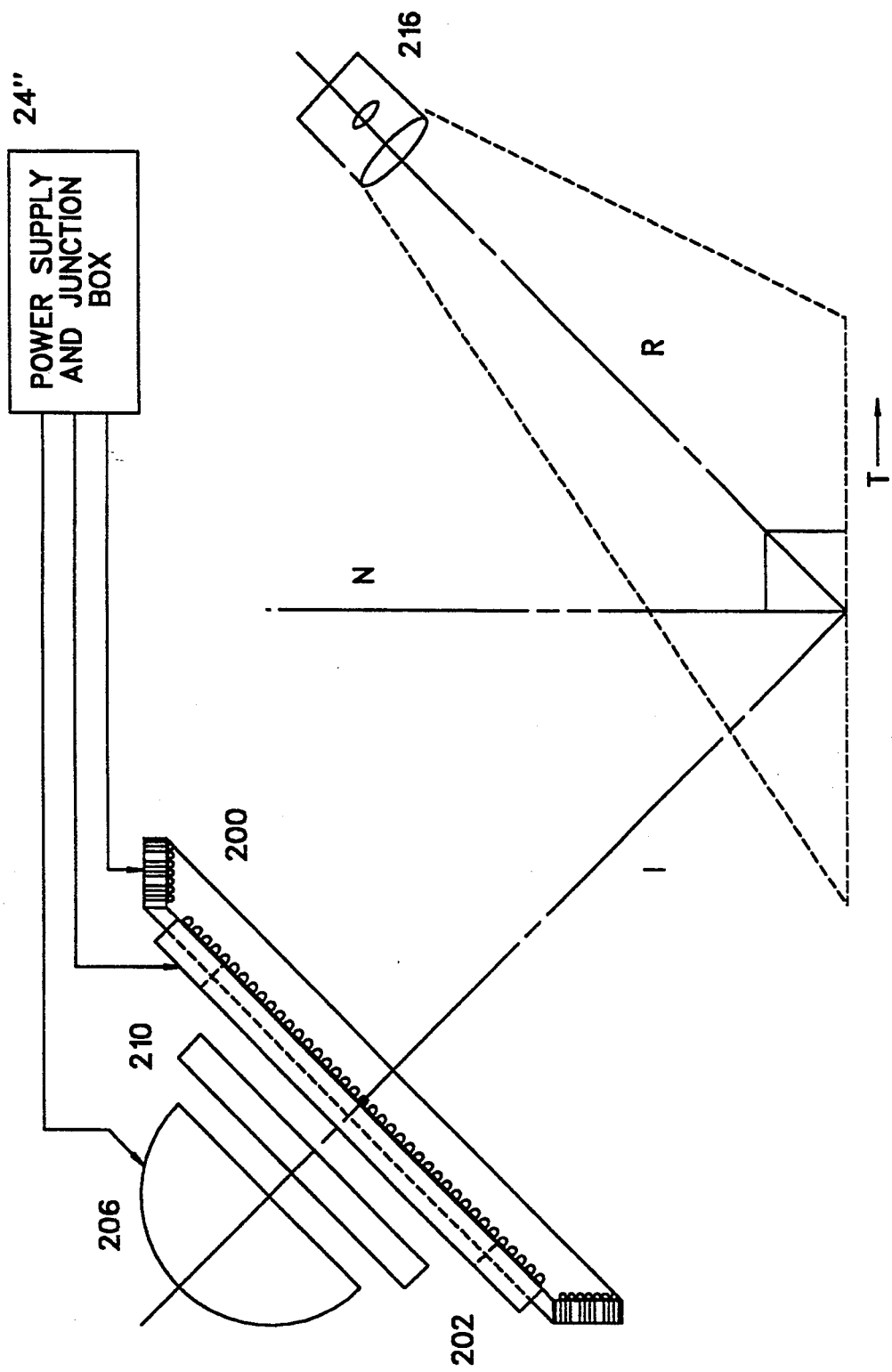
FIG. 12 illustrates several variations of a system including banked LEDs with varied angles between lenses, an optional hybridized conventional source light and a camera employing a perspective control lens.

Turning now to FIG. 12, additional modifications to the subject system are described. In this illustration, illumination is provided from several sources. Solid-state, LED illumination is provided from a first circular ring array 200 and a second, circular ring array 202. The ring 200 is illustrated in cut-away form for ease in visualization. In this particular illustration, LEDs of the first ring array 200 are chosen so as to provide a selected wavelength range, such as amber. Those LEDs of the array 202 are chosen to provide a second spectrum range, such as red. Accordingly, FIG. 12 provides additional illustration as to structured or engineered lighting. This evidences angle, intensity, and spectrum of illumination constituents. As with the earlier illustrations, it is to be appreciated that specific applications may dictate incorporation of various combinations of LEDs, both spectrally and relative quantities, within or between the arrays 200 and 202.

An additional illumination example is also evidenced by FIG. 12. A conventional lighting source is suitably implemented as a supplemental light generator. Such conventional illumination is suitably formed of incandescent, fluorescent, halogen, or intermittent duty strobe lighting such as inert gas xenon or the like, inert gas, or other similar, non solid-state junction lighting. Such conventional lighting sources provide multiple spectrum illumination. Therefore, this embodiment is optionally provided with a filter 210 which eliminates any undesirable light wavelength from that emanating from conventional source 206.

Light from each of the arrays 200 and 202, as well as that from the conventional source 206, is directed to a lighting or viewing area indicated generally at 212.

In conventional lighting arrangements, a camera, more specifically a lens thereof, is disposed at some point within the illumination source, such as in the middle of rings 200 and 202. Typically, the camera is mounted so as to have its lens axis orthogonally along a normal N of a direction of travel T of a specimen. This relative orientation allows for a non-distorted image of a specimen to be obtained. Of course, this is to be contrasted with transmissive specimens which allow the camera lens to be located on the other side of the specimen. Problems associated with such relative positioning between the camera and lens and illumination source are particularly deleterious when highly reflective or mirror-like specimens are viewed. With such specimens, an image of the camera lens itself provides substantial artifact on the illuminated image.

A perspective control lens provides well-defined optical properties to counter perspective distortions associated with off-axis placement relative to a specimen. Such a perspective control lens is illustrated generally at 216. Such a lens allows lens 216 to be non-orthogonally secured relative to specimen direction T. The lens 216 is mounted relative to the lighting such that the angle of incidence of direction I of light relative to T is equal to angle of reflection of direction R relative to T. While a single lens 216 is illustrated, it will be appreciated that multiple cameras and filters are advantageously provided, analogous to the embodiments described above. Such has been eliminated from the figure for ease in viewing.

Also illustrated is a power supply junction box 24". This is illustrated to demonstrate control of arrays 200 and 202, as well as conventional light source 206.

The invention has been described with reference to the preferred and alternate embodiments. Obviously, modifications and alterations will occur to others upon a reading and understanding of this specification. It is intended that all such modifications and alterations be included insofar as they come within the scope of the appended claims or the equivalents thereof.

Having thus described our invention, we now claim:

1. An engineered video inspection illumination system comprising:

a first array of light emitting diodes adapted to provide illumination of a plurality of selected wavelength quanta;

first securing means adapted to secure the first array so as to illuminate an associated specimen disposed in an illumination region of the first array;

means for selectively supplying current to the first array so as to generate inspection light therefrom having a selected light constituent of first and second wavelengths; and video receptor means adapted for receiving the inspection light after exposure thereof to the associated specimen.

2. The engineered video inspection illumination system of claim 1 wherein the video reception means includes isolation means for segregating the first and second wavelength quanta of the inspection light into first and second images, respectively.

3. The engineered video inspection illumination system of claim 2 wherein the video receptor means includes first and second video sensors, and wherein the isolation means includes:

a first filter, adapted to filter a first selected wavelength, disposed to intercept the inspection light prior to exposure to the first video sensor; and a second filter, adapted to filter a selected wavelength, different than the first selected wavelength, disposed to intercept the inspection light prior to exposure of the second video sensor.

4. The engineered video inspection illumination system of claim 2 wherein the video receptor means includes first and second spatially separated video sensors, and wherein the isolation means includes a prism disposed to intercept the inspection light prior to exposure of the first and second spatially separated video sensors.

5. The engineered video inspection illumination system of claim 2 wherein the video receptor means includes first and second spatially separated video sensors, and wherein the isolation means includes a diffraction grating disposed to intercept the inspection light prior to exposure of the first and second spatially separated video sensors.

6. The engineered video inspection illumination system of claim 2 wherein the light emitting diodes of the first array are composed of visible light generating devices.

7. The engineered video inspection illumination system of claim 1 wherein the first array includes:

a first plurality of diodes, each of which provide light at a first wavelength quanta; and a second plurality of diodes which provide light at a second wavelength quanta.

8. An engineered video inspection illumination system comprising:

a first array of light emitting diodes adapted to provide illumination of a plurality of selected wavelength quanta, wherein the first array includes a plurality of multi-spectrum diodes;

first securing means adapted to secure the first array so as to illuminate an associated specimen disposed in an illumination region of the first array; and means for selectively supplying current to the first array so as to generate inspection light therefrom having a selected light constituent of first and second wavelengths.

9. An engineered video inspection system comprising:

a first array of light emitting diodes adapted to provide illumination of a plurality of selected wavelength quanta;

first securing means adapted to secure the first array so as to illuminate an associated specimen disposed in an illumination region of the first array;

means for selectively supplying current to the first array so as to generate inspection light therefrom having a selected light constituent of first and second wavelengths;

means for receiving a displacement signal representative of a linear displacement of the associated specimen relative to the first array over a selected scan period; and controller means for selectively supplying a current pulse to the light emitting diodes during the scan period in accordance with the displacement signal such that each of a plurality of generally linear sections of the associated specimen is illuminated a plurality of times by the light emitting diodes.

10. The engineered video inspection illumination system of claim 9 further comprising:

video receptor means adapted for receiving the inspection light after exposure thereof to the associated specimen.

11. The engineered video inspection illumination system of claim 10 wherein the video receptor means includes isolation means for segregating the first and second wavelength quanta of the inspection light into first and second images, respectively.

12. The engineered video inspection illumination system of claim 11 wherein the video receptor means includes first and second video sensors, and wherein the isolation means includes:

a first filter, adapted to filter at least a first selected wavelength, disposed to intercept the inspection light prior to exposure to the first video sensor; and a second filter, adapted to filter at least a selected wavelength, different than the first selected wavelength, disposed to intercept the inspection light prior to exposure of the second video sensor.

13. The engineered video inspection system of claim 12 wherein the light emitting diodes of the first array are composed of visible light generating devices.

14. The engineered video inspection illumination system of claim 11 wherein the video receptor means includes first and second spatially separated video sensors, and wherein the isolation means includes a prism disposed to intercept the inspection light prior to exposure of the first and second spatially separated video sensors.

15. The engineered video inspection illumination system of claim 11 wherein the video receptor means includes first and second spatially separated video sensors, and wherein the isolation means includes a diffraction grating disposed to intercept the inspection light prior to exposure of the first and second spatially separated video sensors.

16. The engineered video inspection illumination system of claim 9 wherein the first array includes:

a first plurality of diodes, each of which provide light at a first wavelength subset; and a second plurality of diodes which provide light at a second wavelength subset.

17. The engineered video inspection illumination system of claim 9 wherein the first array includes a plurality of multi-spectra diodes.

18. A method of multiple wavelength video inspection specimen illumination comprising the steps of:
  selectively providing a current pulse to first array of light emitting diodes adapted to provide illumination of a plurality of selected wavelength quanta, the step including selectively supplying current to the first array so as to generate inspection light therefrom having a selected light constituent of first and second wavelengths;
  illuminating an associated specimen disposed in an illumination region of the first array with light of the first array;
  receiving a displacement signal representative of a linear displacement of an associated specimen relative to the array; and
  selectively providing the current pulse so as to provide the current pulse in accordance with the displacement signal.

19. The method of multiple wavelength video inspection of claim 18 further comprising the step of selectively providing the current pulse so as to provide the illumination with a specified spectral content.

20. The method of multiple wavelength video inspection of claim 19 further comprising the step of selectively providing the current pulse so as to provide the illumination with a specified duration.

21. The method of claim 20 wherein the step of selectively providing includes the step of selectively supplying the current to the first array so as to generate inspection light composed of visible light.

22. An engineered video inspection illumination system comprising:
  a first array of light emitting diodes adapted to provide illumination of at least one selected wavelength range;
  a second light source, formed from at least one conventional lamp, adapted to provide illumination of a plurality secondary wavelengths;
  first securing means adapted to secure the first array and the second light source so as to illuminate an associated specimen disposed in an illumination region of the first array;
  means for selectively supplying current to the first array so as to generate inspection light therefrom having a selected light constituent of first and second wavelengths; and
  video receptor means adapted for receiving the inspection light after exposure thereof to the associated specimen.

23. The engineered video inspection illumination system of claim 22 wherein the video receptor means includes isolation means for segregating the first and second wavelength of the inspection light into a first image and at least a second wavelength of the plurality of secondary wavelengths into a second image.

24. The engineered video inspection illumination system of claim 23 wherein the video receptor means includes first and second video sensors, and wherein the isolation means includes:
  a first filter, adapted to filter a first selected wavelength, disposed to intercept the inspection light prior to exposure to the first video sensor; and
  a second filter, adapted to filter the second selected wavelength, different than the first selected wavelength, disposed to intercept the inspection light prior to exposure of the second video sensor.

25. The engineered video inspection illumination system of claim 24 wherein the light emitting diodes of the first array are composed of visible light generating devices.

26. An engineered video inspection illumination system comprising:
  a first array of light emitting diodes adapted to provide illumination of at least one selected wavelength range;
  first securing means adapted to secure the first array so as to illuminate an associated specimen disposed in an illumination region of the first array;
  means for selectively supplying current to the first array so as to generate inspection light therefrom having a selected light constituent of at least a first wavelengths;
  video receptor means adapted for receiving the inspection light after exposure thereof to the associated specimen;
  means for securing the video receptor means so as to be non-orthogonal to a direction of travel of the associated specimen relative thereto; and
  the video receptor means including a perspective control lens having its field of view directed to the illumination region.

27. The engineered video inspection system of claim 26 wherein:
  the first array of light emitting diodes includes means for providing illumination of at least a second selected wavelength range;
  the means for selectively supplying current to the first array includes means for selectively supplying current thereto so as to generate inspection light therefrom having a selected light constituent of the second wavelength range.

28. The engineered video inspection illumination system of claim 27 wherein the video receptor means includes isolation means for segregating light of the first and second wavelength range into first and second images, respectively.

29. The engineered video inspection illumination system of claim 28 wherein the video receptor means includes first and second video sensors, and wherein the isolation means includes:
  a first filter, adapted to filter a first selected wavelength, disposed to intercept the inspection light prior to exposure to the first video sensor; and
  a second filter, adapted to filter a selected wavelength, different than the first selected wavelength, disposed to intercept the inspection light prior to exposure of the second video sensor.

30. The engineered video inspection illumination system of claim 29 further comprising:
  means for receiving a displacement signal representative of a linear displacement of the associated specimen relative to the first array over a selected scan period; and
  controller means for selectively supplying a current pulse to the light emitting diodes during the scan period in accordance with the displacement signal such that each of a plurality of generally linear sections of the associated specimen is illuminated a plurality of times by the light emitting diodes.

31. The engineered video inspection system of claim 30 wherein the light emitting diodes of the first array are composed of visible light generating devices.

32. The engineered video inspection system of claim 1 wherein the first array of light emitting diodes includes means for providing one of the plurality of selected wavelength quanta in the visible spectrum and another of the plurality of selected wavelength in the invisible spectrum.

33. The engineered video inspection system of claim 32 wherein the selected wavelength quanta in the invisible spectrum is infrared.

34. The engineered video inspection system of claim 32 wherein the selected wavelength quanta in the invisible spectrum is ultraviolet.

35. The engineered video inspection system of claim 32 further comprising video receptor means adapted to receiving the inspection light after exposure thereof to the associated specimen, the video receptor means including isolation means for segregating the first and second wavelength quanta of the inspection light into first and second images, respectively.

36. The engineered video inspection system of claim 1 wherein the first array of light emitting diodes includes means for providing the plurality of selected wavelength quanta in the invisible spectrum.

37. The engineered video inspection system of claim 36 wherein the selected wavelength quanta in the invisible spectrum is infrared.

38. The engineered video inspection system of claim 36 wherein the selected wavelength quanta in the invisible spectrum is ultraviolet.

39. The engineered video inspection system of claim 36 further comprising video receptor means adapted to receiving the inspection light after exposure thereof to the associated specimen, the video receptor means including isolation means for segregating the first and second wavelength quanta of the inspection light into first and second images, respectively.

* * * * *